(12) United States Patent
Berndt et al.

(10) Patent No.: US 11,749,087 B2
(45) Date of Patent: Sep. 5, 2023

(54) PROCESS, SYSTEM AND ALARM MANAGEMENT SYSTEM FOR ANALYZING DATA OF A MOBILE GAS MEASURING DEVICE

(71) Applicant: Dräger Safety AG & Co. KGaA, Lübeck (DE)

(72) Inventors: Malte Berndt, Lübeck (DE); Christof Rodehorst, Lübeck (DE); Raphael Maas, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 17/679,573

(22) Filed: Feb. 24, 2022

(65) Prior Publication Data
US 2022/0284791 A1    Sep. 8, 2022

(30) Foreign Application Priority Data
Mar. 2, 2021   (DE) .................... 10 2021 105 008.1

(51) Int. Cl.
| | | |
|---|---|---|
| G08B 21/00 | (2006.01) |
| G08B 21/14 | (2006.01) |
| G01N 33/00 | (2006.01) |
| G08B 7/06 | (2006.01) |
| G08B 21/18 | (2006.01) |

(52) U.S. Cl.
CPC ......... *G08B 21/14* (2013.01); *G01N 33/0063* (2013.01); *G08B 7/06* (2013.01); *G08B 21/182* (2013.01)

(58) Field of Classification Search
CPC ........ G08B 21/14; G08B 7/06; G08B 21/182; G08B 21/0423; G01N 33/0063
See application file for complete search history.

(56) References Cited

U.S. PATENT DOCUMENTS

| | | | | |
|---|---|---|---|---|
| 11,519,809 | B2 * | 12/2022 | Ziolkowski | ............. G01M 3/20 |
| 2004/0233855 | A1 * | 11/2004 | Gutierrez | ................ H04L 45/00 |
| | | | | 370/252 |
| 2005/0275532 | A1 * | 12/2005 | Ferri | ...................... H04L 67/12 |
| | | | | 340/870.11 |

(Continued)

FOREIGN PATENT DOCUMENTS

| | | |
|---|---|---|
| DE | 102017124095 A1 | 4/2018 |
| EP | 2339556 A1 | 6/2011 |

*Primary Examiner* — Ojiako K Nwugo
(74) *Attorney, Agent, or Firm* — McGlew and Tuttle, P.C.

(57) ABSTRACT

A process and system analyze data provided by a mobile gas measuring device (3a) for generating an alarm. An alarm management system implements the process and system. The measured data are transmitted to another gas measuring device and/or to a data processing unit (1) and are compared to a limit value. If a limit value violation is detected, an alarm control signal is generated for implementing an instruction for action. A hazard potential is determined and is assigned to the limit value violation in the gas measuring device, the other device, and/or in the data processing unit, taking into consideration weighted influencing variables. Upon a first limit value violation and a second limit value violation being determined, the hazard potentials of these violations are compared and a prioritization is determined based on the comparison. The generation of the alarm control signals is carried out based on the determined prioritization.

18 Claims, 2 Drawing Sheets

(56) References Cited

U.S. PATENT DOCUMENTS

| | | |
|---|---|---|
| 2006/0082462 A1 | 4/2006 | Crook |
| 2014/0051459 A1* | 2/2014 | Gonia ................ G01S 5/0036 |
| | | 455/456.1 |
| 2017/0193790 A1 | 7/2017 | Cornwall |
| 2017/0303187 A1* | 10/2017 | Crouthamel ...... H04W 52/0235 |
| 2018/0107188 A1 | 4/2018 | Nixon et al. |
| 2018/0301013 A1* | 10/2018 | Wang ................ G01N 33/0075 |

* cited by examiner

Fig.2

PROCESS, SYSTEM AND ALARM MANAGEMENT SYSTEM FOR ANALYZING DATA OF A MOBILE GAS MEASURING DEVICE

CROSS REFERENCE TO RELATED APPLICATIONS

This application claims the benefit of priority under 35 U.S.C. § 119 of German Application 10 2021 105 008.1, filed Mar. 2, 2021, the entire contents of which are incorporated herein by reference.

TECHNICAL FIELD

The present invention pertains to a process as well as to a system for analyzing data that are provided by at least one mobile gas measuring device and are used for alarm generation for a person. Further, the present invention pertains to an alarm management system, in which the process or system is implemented. In the process being described and in the system, measured data are generated by a mobile gas measuring device and are transmitted to another mobile gas measuring device and/or to a data processing unit. Furthermore, a comparison of the measured data with at least one limit value is performed, and an alarm control signal is generated for taking an action in case an inadmissible violation of the limit value is determined.

TECHNICAL BACKGROUND

The monitoring of production sites, e.g., refineries, chemical plants, steel mills or mines, wherein mobile gas measuring devices are used for the protection of the employees working at the respective production sites, is known, in general, from the state of the art. Risks due to toxic gases or vapors, an explosive, especially oxygen-rich or low-oxygen atmosphere in the area around the user of the device, are detected by means of the mobile gas measuring devices and an alarm generation is triggered.

Mobile gas measuring devices have for this reason, on the one hand, suitable sensors for detecting the concentrations of gases or gas mixtures and, on the other hand, elements that notify the device user in case of a potentially hazardous situation and/or generate an alarm for the device user.

Contrary to stationary gas measuring devices, mobile gas measuring devices are usually carried along by a user of the measuring device within the production site and are thus moved and are used for personal protection or for remote measurement in crowded spaces. Further, they are used at times for monitoring rooms or in the vicinity of electrical devices in potentially explosive work areas, for example, when welding or soldering operations are carried out. An essential feature of mobile gas measuring devices is that the user of the measuring device is informed and/or an alarm is generated for the user if toxic gases or vapors reach a hazardous concentration, if an explosive atmosphere has formed or there is a lack of oxygen or an inadmissible excess of oxygen. The measured data generated are stored, as a rule, in an internal memory of the device at least for a certain time.

A system for monitoring gas concentrations in a monitored area, in which a plurality of gas measuring devices are used, is known in this connection from US 2017/0193790 A1. The gas measuring devices transmit the generated measured data to a central data processing unit of a control room, in which, among other things, an alarm event that has actually occurred shall be detected. It is an essential feature of the technical solution being described that, on the one hand, the measurement intervals of a gas measuring device are reduced if the detected measured values are approaching a limit value and, on the other hand, additional gas measuring devices located in the vicinity are likewise activated or the measurement intervals are reduced in these gas measuring devices as well.

Generated measured data, the status of the measurement devices as well as data that contain information on alarms that have occurred within a measurement time period or errors that have developed are often usually transmitted in a wireless manner during the use of modern mobile gas measuring devices to a central data processing unit. It is possible in this manner to carry out a monitoring of people centrally and to establish a contact when needed and to check whether the person requires assistance or even to take suitable actions directly for the protection of the person.

It should be taken into consideration in this connection that up to 5,000 employees may be working simultaneously at large production sites, e.g., in steel mills. Hundreds of people, who must be monitored, may also be working in different work areas in some cases simultaneously in refineries, chemical plants or mines. Especially in respect to the monitoring systems that are used at such large production sites, the data generated by mobile gas measuring devices, especially alarm information, are usually transmitted on a regular basis to a central office, at which a suitable data processing unit is located. The transmitted data can be visualized in this manner in the control room, and alarms, pop-up messages or SMS messages are displayed directly on a map. Moreover, it is possible to store data that pertain to alarms and errors that have occurred and to use them for a later evaluation and analysis of the event of an incident or damage.

Even if different alarm limit or threshold values, which are set in the device or in a central data processing unit, are set in the monitoring systems used, precisely the occurrence of a plurality of alarms in a control room of larger production sites represents a problem at times. Especially if a plurality of alarms occur simultaneously in a control room, it is often not easy for a person on duty to make a decision as to the order in which the individual alarms must be processed and suitable actions must be taken. It should be borne in mind in this connection that different measured values, map sections and additional information must be detected and it is difficult to specify the importance and a suitable processing of actions in respect to the different alarms. It is likewise impossible with the prior-art systems to show changes in the hazardous area in a timely manner and to take them into consideration when taking appropriate actions. In addition, alarms are often generated in non-critical situations, so that, in particular, staff being monitored are desensitized because of frequently occurring irrelevant alarms and there is a risk of development of a so-called alarm fatigue.

SUMMARY

Based on the technical solutions known from the state of the art as well as on the above-described problems, a basic object of the present invention is to provide a process, a monitoring system as well as an alarm management system, during the use of which actions can be taken in respect to different alarms, occurring in a common time period or during overlapping time periods (e.g., occurring essentially simultaneously), at a central office rapidly, with reasonable effort and nevertheless with high accuracy. Such a process or system should be configured such that it is also possible to minimize the manpower requirement without having to accept losses in terms of the protection of the employees working at the production site. The taking of suitable actions for informing, assisting or rescuing people, who are located in different hazardous areas from which alarms are coming, shall be carried out with a high accuracy and in the suitable as well as necessary chronological order. It should be possible in this connection to offer a suitable action recommendation possibly for each alarm, taking into consideration different influencing variables and defined parameters, and a chronological prioritization additionally takes place.

Furthermore, it shall advantageously be possible to be able to respond to a corresponding change in the situation rapidly and reliably in case of a changing hazardous situation, e.g., when a person is moving out of the hazardous area and to have the ability possibly to interrupt actions already taken or at least to adapt them to the changed situation. An action recommendation and above all the associated prioritization for a necessary action should be able in this manner to be adapted continuously, so that it is possible to respond to changed conditions in a timely manner.

In view to the different production sites, at which a suitable monitoring system shall be used, i.e., for example, in steel mills, chemical plants, refineries, mines, drilling or extraction platforms or mines, it shall further be possible for a monitoring system or process used correspondingly to be able to be adapted without major effort, for example, by an operator of the system, to user-specific requirements and parameters of a plant. No or only minor changes should be necessary for this on the hardware components being used.

Another object to be accomplished is to take into consideration location-specific information, e.g., on the area from which an alarm originates, i.e., for example, on whether this alarm originates from a workshop, from a hazardous area, from an entry area, from an interior space or from an outer surface, when necessary actions are taken, as well as to take into consideration current measured data originating from the hazardous area. Further, it is desirable to process information arriving at a central office, especially data that have led to the triggering of an alarm, such that this information can be made available for a later analysis or for further assistance actions, which are necessary after conclusion of a rescue mission, e.g., for medical actions.

The above-described object is accomplished with a process in accordance with the invention as well as with a system for measuring the concentration of at least one gas (a gas and/or a gas mixture) in a monitored area in accordance with the invention. An alarm management system, which accomplishes the underlying object of the present invention, is further provided in accordance with the invention. A preferred implementation of such an alarm management system in specific industrial production plants, a mine and/or of a power plant is advantageously provided. Advantageous embodiments of the present invention will be explained in more detail in the following description partially with reference to the figures.

The present invention pertains to a process for analyzing data that are provided by at least one mobile gas measuring device with the aim of generating alarms for people as needed, wherein the following process steps are provided:
  generation of measurement data by at least one mobile gas measuring device on the basis of at least one measurement of a gas concentration in a monitored area and transmission of the measured data to at least one additional mobile gas measuring device and/or to a central data processing unit as well as
  comparison of the measured data with at least one limit value stored in the mobile gas measuring device, in an additional gas measuring device and/or in the central data processing unit and generation of an alarm control signal suitable for taking an action by the additional gas measuring device and/or by the central data processing unit when an inadmissible value higher or lower than the limit value is determined.

The process according to the present invention is characterized in that a hazard potential is determined and is assigned to the limit value violation in the mobile gas measuring device, in the additional gas measuring device and/or in the central data processing unit in case of a determined limit value violation, which is caused by the overshooting or undershooting of the limit value, taking weighted influencing variables into consideration. Further, as soon as a first limit value violation and at least a second limit value violation are determined simultaneously in time or during a common time period or during overlapping time periods, the hazard potentials of the first limit value violation and of the at least one second limit value violation are compared with one another and a prioritization is determined on the basis of the comparison, wherein the generation of the alarm control signals for the first limit value violation and for the at least one second limit value violation is carried out such that the set prioritization is taken into consideration. The prioritization is defined in this connection as the determination of different aspects of importance for the individual hazardous situations, which are based on a limit value violation, and which are used as the basis for the chronological sequence of the taking of suitable actions. It is thus essential for the process according to the present invention that for every individual alarm event, which is based on a limit value violation, a hazard potential is determined, which ultimately corresponds to a hazard that is present at the time of generation of an alarm control signal for a gas measuring device user or for a person, who is located in the area around the mobile gas measuring device, which gas measuring device has transmitted the measured data that have led to the generation of an alarm control signal.

The individual hazard potentials of the hazardous situations or alarm events are set on the basis of weighted influencing variables, which may preferably be properties of a work area, of necessary actions, of a gas measuring device user and/or of a plant part arranged in the work area. Necessary assistance or rescue actions, physical properties of a device user, spatial conditions in the work area, plants present on site and/or situation to be expected on site, especially an existing or presumable toxicity, explosiveness or combustibility of the gas concentration encountered in the work area, are especially preferably used as weighted influencing variables.

If at least two limit value violations, which lead each to the generation of an alarm control signal, are detected at a time or within a time period, a hazardous situation is thus identified, which is determined in the form of a hazard potential as a comparable value that can be processed for data technology, especially by calculation, by taking into consideration the weighted influencing variables for the individual limit value violations, which are ultimately alarm events each. Based on the determined hazard potentials, a comparison of different hazardous situations, which comparison can be made objective, is possible, so that the different hazardous situations are put into a relation to one another, and a prioritization can be set rapidly, as needed and by taking into consideration the current situation for processing the alarms, wherein this prioritization forms the basis for the taking of necessary actions. If the situation changes on site, for example, based on additionally occurring hazards, which are detected by means of the transmitted measured values, the hazard potential of the hazardous situation, which is assigned to the respective limit value violations, changes as well. It is possible in this manner to respond to the changed situation in the hazardous area rapidly and as needed. In particular, the actions taken, e.g., the assisting personnel sent to the site of the hazard and/or requested devices, can be adapted to the changed situation. It is, of course, likewise possible to respond in a suitable manner in case of a reduction of the hazard potential and, e.g., to withdraw the assisting or rescue team, which may already have been alerted, from the alarm event. In addition, it is pointed out that the taking of suitable actions may be both a process carried out by people and a process initiated in an automated manner, for example, the switching on of ventilation for feeding fresh air. Furthermore, an alarm control signal may be both a signal that brings about the output of acoustically, visually and/or haptically perceptible information or alarm generation for at least one person and/or the preferably automated actuation of systems, alarm generation elements, control units and/or display units.

The type and/or the degree of a health hazard arising from a substance, a measured value, especially a maximum measured value, a time period elapsed since the detection of a limit value violation and/or generation of an alarm control signal, an average measured value detected since the detection of a limit value violation and/or generation of an alarm control signal, and a trend prediction, which is determined, for example, on the basis of the slope of a measured curve, are preferably taken into consideration in the weighting of the influencing variables used for setting the hazard potential and hence of the determination of the relevance of the individual influencing variables for the existing hazard and/or for the development of a hazard. Furthermore, the velocity of motion of a person, who is carrying along the mobile gas measuring device, which has triggered the generation of an alarm control signal, or who is at least located in the area around the mobile gas measuring device may be taken into consideration. Corresponding motion data are obtained, e.g., by means of an acceleration sensor and/or of a position sensor, e.g., of a GPS unit, these sensors being generally arranged in the mobile gas measuring device or in a device likewise carried along by the device user, especially in a cell phone. If it is determined in this case that the person located in the hazardous area is not moving any longer, this leads to an increase in the hazard potential compared to the detection of a normal motion. If, by contrast, an especially rapid motion is determined, which may ultimately suggest both a fall and an intentional fleeing motion, it is possible to analyze this motion in a user-specific manner and to take it into consideration for the determination of the hazard potential, especially by both an acceleration and a motion relative to a location being detected and by determining on the basis of these data whether a fall or a presumably intentional fleeing motion is involved. Detection of a specifically directed motion such as walking or running of the person located in the hazardous area is of particular significance in this connection.

Consequently, influencing variables, which can be optionally selected for the determination of a hazard potential, and which can be set and weighted by the user as a function of the conditions prevailing at a production site, are preferably used.

Moreover, it is possible according to a special variant of the present invention that a cell phone being carried by a person is used as a transceiver unit for transmitting the data generated by the mobile gas measuring device to the central data processing unit, for detecting a location, especially via an integrated GPS module and/or for determining a dynamic motion of the gas measuring device user.

Certain influencing variables are mandatory, i.e., absolutely necessary for the determination of a hazard potential in a special embodiment. These may include especially at least one limit value of a gas concentration, a temperature, a radiation dose, a dust concentration, a brightness and/or a loudness, which limit value should not be overshot or undershot, and/or at least one suitable alarm generation threshold value. Corresponding values can preferably be set for different gases, gas mixtures, vapors, substances, work areas and/or selectable events. Moreover, it is advantageous if at least one current measured value and/or a measured value trend is taken into consideration in the determination of a hazard potential.

Provisions are made according to a special variant of the present invention for the gases and vapors to be expected to occur in the hazardous area, especially the toxicity thereof, to be taken into consideration as influencing variables in the determination of the hazard potential. It is significant in this case, but also in general, in the determination of a hazard potential that the measured values, calculated values, hazard categories and/or other data, which are used as the basis for the determination of a variable or of a parameter of an influencing variable, be comparable.

If the hazard existing based on a gas present in the hazardous area is used as the influencing variable, the concentration of the gas is determined at first and is made available for processing in the unit ppm. Based on the type and the concentration of the gas, a value is calculated in the central data processing unit in % immediately dangerous to life and health (% IDLH) and it is available for further processing.

For example, a concentration of 12 ppm CO corresponds here to a value of 1% IDLH, because the IDLH is currently set at 1,200 ppm. In comparison to this, a gas concentration of 10 ppm of chlorine gas ($Cl_2$) corresponds to a value of 100% IDLH, because the IDLH for chlorine gas is currently set at 10 ppm.

It is thus possible according to a special exemplary embodiment to make the gas concentration measured values of different toxic gases or gas mixtures comparable when using a gas concentration on site as an influencing variable and to determine for the influencing variable "gas concentration" a value that is then weighted and is used together with other weighted influencing variables for the determination of a hazard potential, which is a parameter of the hazard that is currently present for a person located in the hazardous area.

An optional influencing variable or a plurality of optional influencing variables, which can preferably be selected by a user as a function of the conditions present at a production site, is/are provided in another special variant of the present invention. Optional influencing variables are also taken into consideration in the determination of the hazard potential if the user selects these optional influencing variables.

For example, the location of a mobile gas measuring device and/or of a person, who is themself carrying this device, may be selected as a special influencing variable. In order to obtain a parameter for the influencing variable "location," hazard levels with specific hazard values are assigned to different work areas. It may be provided, for example, in this connection that potential hazard areas are marked by the user on a map and are assigned to different hazard levels. Safe work areas of a low hazard level can be distinguished at least approximately in this manner from work areas with a medium hazard level and from work areas with a high hazard level. The manner in which the data made available by a mobile gas measuring device are processed and/or the form in which these data are taken into consideration can be adapted in this manner as needed, for example, to the requirements prevailing in a work area or maintenance area, in a hazardous area, which is entered only with the use of a respirator, and/or to the requirements prevailing in an automatically ventilated area, also taking into account the size of the room in question. Furthermore, in an automated manner, historical data, which show, e.g., locations with frequent alarm activity and hence with a high hazard level, may be distinguished from other locations, at which high measured values may, for example, often be detected, but these nevertheless decrease very rapidly. Provisions are made according to a very special variant of the present invention for the system to be complemented by artificial intelligence such that an accurate analysis can be carried out in respect to the error and accident frequency in different production areas on the basis of the measured data obtained in the different zones and/or errors or alarms that have occurred. Risk estimates can likewise be carried out effectively and with a high accuracy, and the monitoring system and the functionality of the gas measuring devices themselves can be optimized on the basis of the available data and the safety can be increased for the employees. The location of a mobile gas measuring device is preferably indicated in this case on the basis of GPS coordinates, and location-specific information is transmitted by the mobile gas measuring device itself or by a transceiver unit, which is likewise carried along, for example, a cell phone, to the central data processing unit. Other monitoring technologies are additionally suitable for detecting and/or defining the location from which the measured data triggering the alarm originate.

Another influencing variable used preferably pertains to the motion profile of a person. Again, different hazard levels can be set here as well for the influencing variable "motion profile" and be taken into consideration in the determination of the hazard potential. The direction in which a user of a mobile gas measuring device is moving is preferably taken into consideration in setting a hazard level. It is significant in this connection, for example, whether the measuring device user is moving, for example, in the direction of a flight point, i.e., to a safe area or in the direction of a hazardous area or else whether he is remaining in the hazardous area.

The influencing variable "constitution of the device user" is used as an additional influencing variable, which is used in an advantageous manner and which can be taken into consideration in a weighted manner in the determination of a hazard potential. The value of this influencing variable depends here on the physical properties of the device user located in the hazardous area, such as the pulse rate, respiration rate and/or body temperature. Depending on whether the corresponding physical parameters are in a normal range or else in a range different from the normal range, a value can be set for this influencing variable.

Basically person-specific data, e.g., age, pre-existing conditions and/or physical properties, for example, height or body weight, may likewise be taken into consideration in the determination of a value for the influencing variable "constitution of the device user" or form the basis for setting a value for an additional influencing variable.

According to another embodiment, provisions are made for also taking into consideration in the determination of a value for an influencing variable "surrounding situation" the situation occurring in the area around the hazardous area, for example, the number of people located in a hazardous area from which the alarm generation originates, the number and the type of the alarms having occurred in adjoining areas and/or the number of people who are located in the area around the hazardous area with or without alarm generation. The hazard potential can be set in this manner such that the people who may either come to the rescue of the person located in the hazardous area from which the alarm is coming or else who also require assistance are taken into consideration.

Furthermore, it is possible that a user sets an influencing variable whose value varies as a function of the presence of certain gases, gas mixtures, vapors and/or gas groups. The values of this influencing variable could be set, for example, as a function of a gas to a defined gas group, so that the danger of toxic gases, of an oxygen deficiency, of combustible gases or of an explosive atmosphere can be put into a relationship to one another in the manner desired by the user, especially by assigning different values to the individual groups depending on their hazard classification.

Provisions are made according to another special embodiment of the present invention for the type and the extent of the equipment of the people who are located in the hazardous area, e.g., tools, protective gear and/or measuring devices, to serve as the basis for the determination of a value for an influencing variable. It is possible in this case to take it into consideration whether a measuring device user carries, for example, a respirator or at least an escape hood. This would reduce the value of the influencing variable "equipment" compared to a person who is not carrying along protective gear and therefore also lead to a reduction of the hazard potential. Furthermore, the properties of protective gear used by a gas measuring device user, i.e., the hazards against which the protective gear offers protection, are taken into consideration. Thus, it is taken into consideration, for example, that, e.g., a fire escape hood or an oxygen self-rescuer offers protection for a certain time only or up to a certain composition of the surrounding atmosphere, whereas a full-face mask offers better protection. It is advantageous in this case as well if the relevance of this special influencing variable for the overall hazard potential increases when the remaining duration of protection decreases.

Moreover, it is advantageous to take into consideration the type of the work carried out or planned in a hazardous area as an influencing variable in the determination of a hazard potential. If, for example, welding operations or machining activities, which may lead to sparking, are planned, this can be taken into consideration in the determination of a value for the "working" influencing variable and possibly lead to an increase in the hazard potential assigned to the work area in the event of an alarm.

According to a special variant of the present invention, the type and/or the number of auxiliary devices available in the area being monitored, e.g., fire extinguishers, fans, safety rooms and/or protective gear, the number of current alarms in the monitored area or in an area of the monitored area, the distance between the location for which a limit value violation was detected and the available rescue team and/or the number and the arrangement of available escape routes are selected as the influencing variable.

On the whole, a plurality of possible influencing variables, which can be set in a user-specific manner as a function of the properties of a production site, especially of the local conditions and of the production or conveying processes being carried out, are available for the determination of a hazard potential. The influencing variables are used in this case to determine a hazard potential for a work area in a hazardous situation, which has led to an alarm generation, wherein the individual influencing variables are weighted concerning their relevance for the risk to life and limb that exists in the hazardous area, especially for the people who are located there, i.e., the significance of the individual influencing variables for the hazardous situation is put into a relationship relative to one another.

Provisions are made according to the present invention for the prioritization carried out by taking into consideration at least two hazard potentials to indicate a chronological sequence, with which the generation of the alarm control signals for taking a suitable action or measure and/or the output of an action recommendation are carried out. Furthermore, it is advantageous if the data processing unit is connected to a central office of a production site and the action recommendations based on the alarm control signals generated are displayed on a display unit corresponding to the prioritization.

According to a special variant, the central data processing unit sends a notification and/or an alarm control signal leading to a notification and/or output of an alarm to at least one mobile gas measuring device, which is located in the hazardous area, in which hazardous area the data on which the generation of the alarm control signal was based were generated, for forming the basis of the set prioritization.

A request signal is sent in an automated manner to members of a rescue team on the basis of the determined hazard potential and/or of the prioritization set in another preferred embodiment of the present invention. Depending on the type of the hazard and the hazard potential, such rescue team members are assisting other rescue team members, for example, a factory fire department or mine rescue unit. If, by contrast, the hazard potential is comparatively low, preferably only a notification of other people located on site, especially of a group leader or shift leader, is carried out. An escalation structure can advantageously be set up in this manner, so that, e.g., an alarm generation is passed on if there is no response to the alarm generation at a first level. If there is no response at the first level, an alarm could be passed on, for example, to a higher level, for which an alarm is actually generated only in case of a higher prioritization. As an alternative or in addition, it is possible that a central office is also informed in case of each alarm or at least one alarm, to which there is no response at one level, is passed on to a central office.

At least one safety device is automatically activated, a machine or system is put out of operation and/or at least one area of a production site is specifically blocked, warned or at least marked in a very special embodiment of the present invention on the basis of the determined hazard potential and/or of the prioritization set. According to this special embodiment a plant part may be put out of operation or blocked by actuation of a control element in an automated manner as a function of a determined hazard potential and/or of the set prioritization. As an alternative or in addition, safety messages may be automatically displayed and/or alarm elements, e.g., alarm lights or alarm sirens, may be activated in a work area of a production site. It is possible in this connection to carry out the corresponding actions as a function of the respective hazard potential determined and to integrate them into a chronological sequence with the taking of other actions, taking into account the prioritization set.

The present invention also pertains otherwise to a system for measuring the concentration of at least one gas in a monitored area with at least two mobile gas measuring devices, with a central data processing unit and with means for unidirectional or bidirectional data transmission between the mobile gas measuring devices and the central data processing unit, wherein the system is suitable for the implementation of a process that is configured in accordance with at least one of the above-described special embodiments.

Furthermore, the present invention also pertains to an alarm management system for managing alarms, which are triggered by the setting of a limit value violation caused by the determination of an overshooting or undershooting of a limit value during the measurements of gas concentrations carried out by means of mobile gas measuring devices in a monitored area. The alarm management system according to the present invention is characterized in that a data processing unit is provided and is set up such that a hazard potential is determined for a limit value violation determined on the basis of the measurement and analysis, taking into consideration weighted influencing variables, which were described above, and the hazard potential is assigned to the limit value violation. Furthermore, as soon as a first limit value violation and at least one second limit value violation are detected simultaneously in time or at least during overlapping time periods or during a common time period, the hazard potentials of the first limit value violation and of the at least one second limit value violation are compared with one another and a prioritization is determined on the basis of the comparison, wherein the generation of the alarm control signals for the first limit value violation and for the at least one second limit value violation is carried out such that the set prioritization is taken into consideration. An alarm management system is thus provided according to the present invention, which makes it possible for users, especially for the person working at a central office, for example, in a control room of a production site, to take suitable actions for assisting and/or rescuing people in a hazardous area, from which the alarm originates, rapidly, reliably and as needed. A respective hazard potential is assigned in this case to the individual alarm events, which are based on the determination of a limit value violation, on the basis of weighted influencing variables, and a prioritization is established for the taking of additional actions as a function of the hazard potentials of the current alarm events without staff performing any action for this.

The alarms can then be processed by means of manual actions taking into consideration the prioritization set in an automated manner, or else suitable actions are taken in an automated manner.

The present invention otherwise pertains to a control room of a refinery, of a chemical plant, of a steel mill, of a mine, of a power plant and/or of another industrial production or conveyor system with an alarm management system configured according to the present invention. The technical features of the special embodiments described in connection with the process according to the present invention as well as with the system according to the present invention can, in turn, be used alone or in combination when such an alarm management system is embodied.

The present invention will be explained in more detail below on the basis of exemplary embodiments with reference to the figures without limitation of the general inventive concept. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
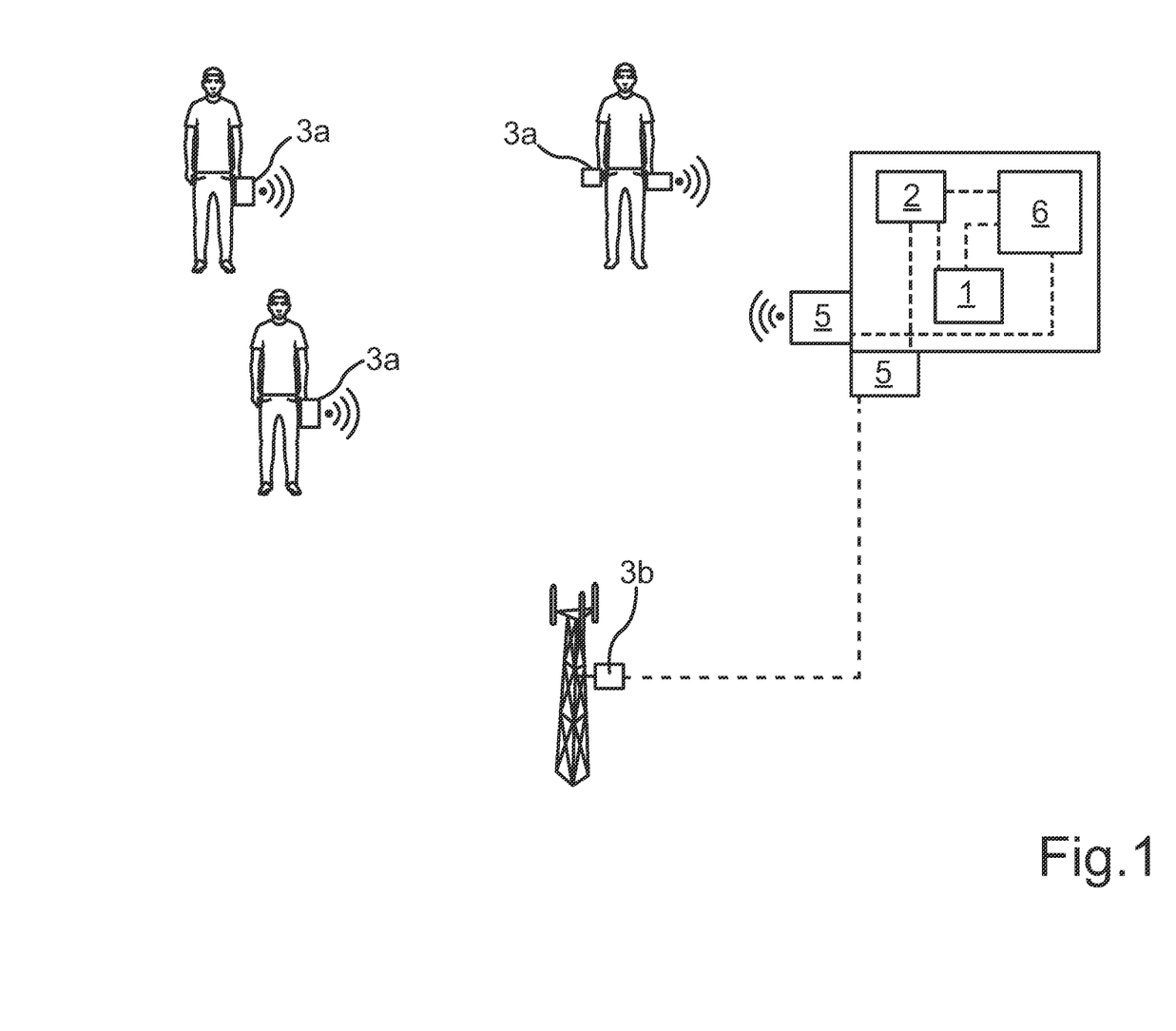
FIG. 1 is a schematic view of a system for monitoring the concentration of at least one gas or gas mixture in a monitored area of a production site.

Referring to the drawings, FIG. 1 schematically shows a system for monitoring the concentration of at least one gas or gas mixture in a monitored area of a production site, in this case a refinery, at which different chemical media are processed, conveyed, produced and/or transferred, especially in the liquid or gaseous form. The system shown schematically is suitable for monitoring the atmosphere in a plurality of work areas of the production site with respect to the presence of toxic gases or vapors, combustible or explosive atmospheres or an oxygen deficit. The monitoring system being shown has mobile and stationary gas measuring devices 3a, 3b, with which the concentration of individual gases or gas mixtures is detected and corresponding data can be transmitted to a central data processing unit 1 of a control room of the production site.

Both mobile and stationary gas measuring devices 3a, 3b are used as gas measuring devices for monitoring the production site shown schematically in FIG. 1. Mobile gas measuring devices 3a are used mainly for the protection of the people working in the work areas and they have suitable sensors in order to detect the concentration of gases or gas mixtures, which are present in the respective work area or may occur in a hazardous concentration. Further, the mobile gas measuring devices 3a have, on the one hand, elements that inform the user of the device in the case of a limit value violation and/or generate an alarm for the user and, on the other hand, they have a transmission unit, which makes possible, at least from time to time, the direct or indirect transmission of the generated data to a suitable transmission interface 5 of the central data processing unit 1.

The stationary gas measuring devices 3b monitor above all special areas or plants in the monitored area of the production site for the presence of toxic, combustible or explosive gases or gas mixtures in order for an alarm generation to take place as rapidly as possible and for countermeasures, e.g., putting the plant out of operation, to be taken as rapidly as possible. The stationary gas measuring devices 3b have for this purpose a sensor or a plurality of sensors. The measured data generated continuously or intermittently are passed on for further processing to a suitable transmission interface 5 of the central data processing unit 1 in the control room of the production site and they are processed there either immediately or after an intermediate storage in a central memory 4.

According to the embodiment shown in FIG. 1, the data generated in the different gas measuring devices 3a, 3b are transmitted to a transmission interface 5 of the central data processing unit 1 in a wireless or wired manner. The data are stored intermediately at least partially in a central memory 4 within the central data processing unit 1 and are analyzed by means of a data analysis unit 2.

It is essential for the system shown in FIG. 1 that the central data processing unit 1 is configured to determine a respective hazard potential based on weighted influencing variables when a limit value violation is determined and that the hazard potentials of the respective limit value violations are compared as soon as at least two limit value violations are determined at the same times or in overlapping time periods or in a same time period, and that the limit value violations and hence the alarm events that have caused the limit value violations are thus prioritized on the basis of this comparison, i.e., they are ranked in respect to the risks existing for the people located in the hazardous area. Furthermore, alarm control signals, which form the basis for the taking of suitable actions or measures, especially the notification of and alarm generation for people and/or assistance and rescue team members, are generated by taking into consideration the prioritization. The suitable actions may be carried out manually by the people on duty of a control room of the production site or in an automated manner by actuating alarm generation elements and/or control elements.

Figure 2:
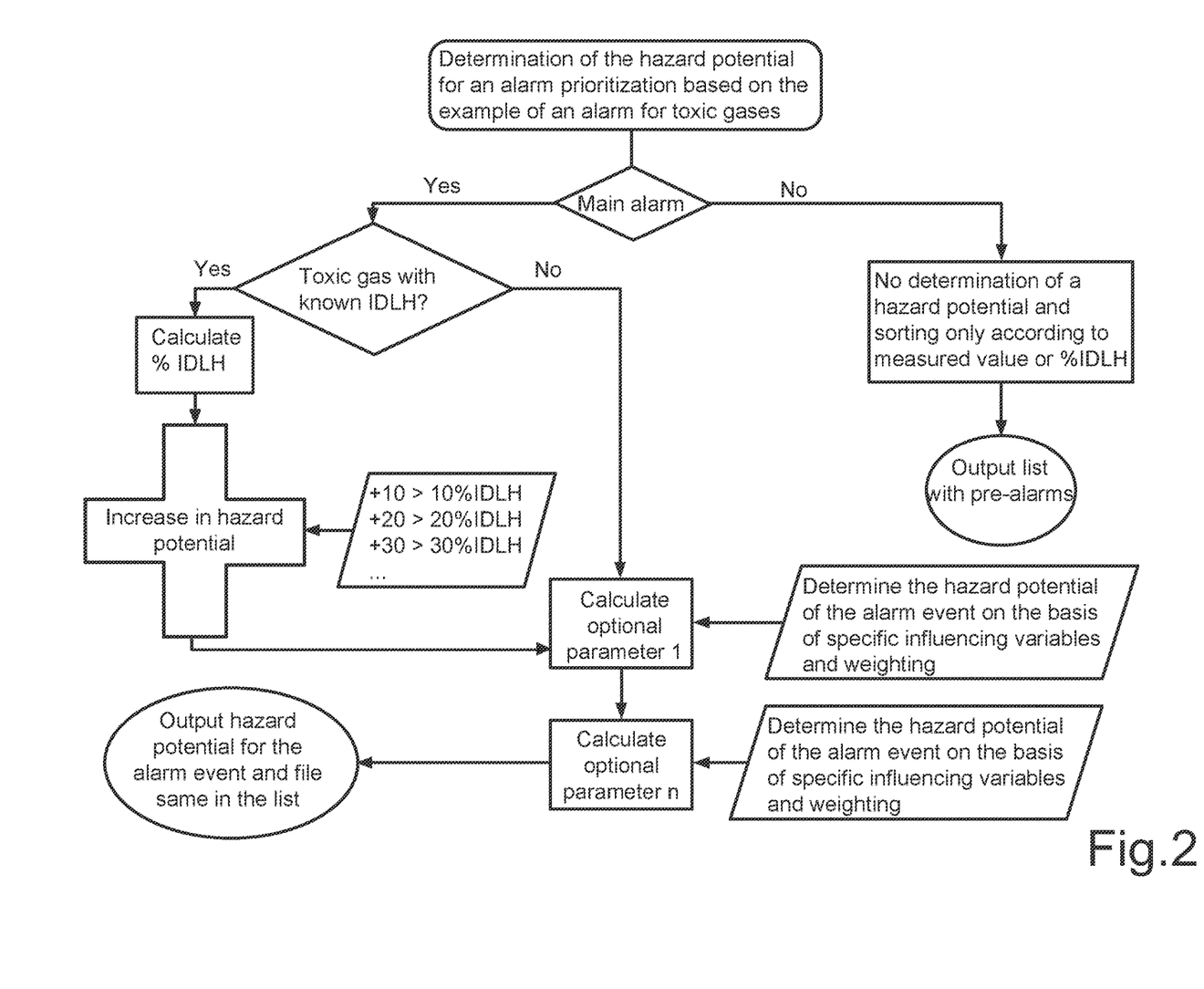
FIG. 2 is a schematic flow diagram of a process for determining the hazard potential of hazardous situations and for prioritizing the hazard potentials at an industrial production site.

FIG. 2 shows in a schematic view the course of the process during the determination of a hazard potential for an alarm occurring at an industrial production site as a function of the measured data transmitted directly or indirectly from mobile gas measuring devices. As soon as a limit value violation is determined, which leads to an alarm generation or to the generation of an alarm control signal, especially the overshooting of a permissible gas concentration, a hazard potential is assigned to the limit value violation that leads to an alarm event by means of the process described. As soon as at least two limit value violations are detected simultaneously or during a common time period or at least during overlapping time periods and the corresponding alarm control signals are generated, the hazard potentials of the two alarm events are compared with one another and are prioritized corresponding to the extent of the determined hazard potential, i.e., they are arranged in a chronological ranking for the processing of the alarms or for the taking of suitable actions.

Depending on the prioritization, which has now been established, suitable actions can be taken in an automated manner or by people working in the control room for averting the hazard, for taking relief actions or for rescuing the people located in the hazardous area. In this connection, that information may be displayed in the control room on a display screen and/or on a map of the production site as a function of the prioritization.

The determination of the hazard potential for an alarm event is carried out such that different influencing variables are taken into considerations, wherein both mandatory influencing variables, i.e., influencing variables that are to be taken into consideration obligatorily, and optional influencing variables are provided. The individual influencing variables are weighted during the determination of the hazard potential in order thus to make it possible to take into consideration the respective significance of an influencing variable for the existing hazard or the changes in this influencing variable during the determination of the hazard potential.

It is further possible in the case of the influencing variables to be used optionally that defined influencing variables are specifically selected or even defined by the user as a function of the on-site conditions.

According to the exemplary embodiment shown in FIG. 2, measured data transmitted wirelessly (in a wireless manner) from mobile gas measuring devices 3a carried along by people in the monitored area reach a central data processing unit 1. It is decided (determined) in a first step in the central data processing unit 1 and/or in the mobile gas measuring device 3a whether a limit value violation, i.e., overshooting or undershooting of a set limit value is present based on the measured data. If no limit value violation has taken place, no hazard potential is determined, and the transmitted measured data are only stored in a central memory 4 and they are available for later evaluations or analyses.

If, by contrast, a limit value violation is determined, which leads to the generation of an alarm control signal, a hazard potential is set at the same time for this alarm event. The overshooting of the permissible concentration of a gas is taken into consideration as a first influencing variable in the exemplary embodiments being described here, and it is checked in a first step whether the existing limit value violation has taken place for a gas with an IDHL value (Immediately Dangerous to Life and Health) being stored in the data processing unit. If an IDLH value is being stored, this value is taken into consideration in the determination of a hazard value for the influencing variable "gas concentration." This hazard value of the influencing variable influences the value of the hazard potential, and the influencing variable is weighted by taking into consideration the other influencing variables, and the significance of the influencing variable for the alarm event is thus taken into consideration. The hazard value of the influencing variable "gas concentration," which hazard value is to be determined, assumes different numerical values in this case as a function of the magnitude of the IDLH value. If the IDLH value is higher than 10% IDLH, the hazard value is 10; if it is higher than 20% IDLH, it is 20; if it is higher than 30% IDLH, it is 30, etc. The higher the hazard value, on the one hand, and the weighting factor for weighting the influencing variable "gas concentration," on the other hand, the stronger is the influence of the influencing variable "gas concentration" on the determination of the hazard potential.

Should no IDLH value be stored for a gas, only the other influencing variables are taken into consideration for the determination of the hazard potential. The other influencing variables used according to the embodiment described are optional influencing variables, which were selected by a user as a function of the on-site conditions. A hazard value is determined at first for each of these influencing variables as a function of measured data or other existing information. This hazard value of an influencing variable is then included in the determination of the hazard potential by taking a weighting into consideration.

For example, the maximum measured value since the triggering of the alarm, an average measured value since the triggering of the alarm, a trend prediction, which is generated especially by determining the slope of the measured curve of a gas concentration, the velocity of motion of a person in the work area in which an alarm event is occurring, the motion profile, especially the direction of the motion of a person, vital data, e.g., the pulse rate or respiration rate or body temperature of a person located in the hazardous area, specific data, e.g., age, pre-existing conditions and the fact that a person belongs to a risk group, the characteristics of the surrounding area, especially the number of people who can offer assistance or who likewise require assistance, the type of the hazardous substance that has triggered the alarm event, existing equipment of the people in the hazardous area and/or planned work or work carried out in the hazardous area may be taken into account by the user as optional influencing variables.

According to the process according to the present invention, certain influencing variables are set at first for the determination of the hazard potential of an alarm event and, as soon as at least two alarm events occur essentially simultaneously in time or in a same time period of in overlapping time periods, the hazard potentials of the alarm events are compared to one another and/or put into a relationship with one another. For example, the fact that the gas present in the hazardous area at an excessively high concentration belongs to a group of gases and vital data of the device user in the hazardous area are taken into consideration in the exemplary embodiment being described here. In respect to the influencing variable "belonging to a gas group," three gas groups are defined at first, to which specific hazard values are, in turn, assigned. A first gas group comprises toxic gases, and it is possible to provide subgroups. Low-oxygen atmosphere belongs to a second group and explosive gases or gas mixtures belong to a third group.

The hazard values, which are assigned to the individual gas groups and which are used later for the calculation, are a parameter of the hazard that develops for the user based on the corresponding gas atmosphere.

The influencing variable "vital data" is likewise divided into the following three hazard classes, to which a hazard value each is then assigned as a function of the respective assumable hazard. The first hazard class pertains to an increased pulse rate, the second to a normal pulse rate and the third to an excessively low pulse rate. The same hazard value is assigned in this case to the first and third groups, because a special hazardous situation can be inferred from both an excessively high pulse rate and from an excessively low pulse rate.

As soon as corresponding hazard values have been determined for all influencing variables used, these are taken into consideration for the determination of the hazard potential of an alarm event, and the individual influencing variables are weighted by taking into consideration the hazard that these represent for the person located in the hazardous area. It is thus conceivable in respect to the exemplary embodiment selected here to take into consideration the influencing variable "belonging to a gas group" with a higher weighting factor in the determination of a hazard potential than the influencing variable "vital data." As was described above, a plurality of influencing variables may be taken into consideration, on the one hand, and it is possible, on the other hand, to set both the individual hazard groups of the influencing variables, the hazard values on which these are based as well as the weighting of the different influencing variables for the determination of the hazard potential of an alarm event in a user-specific manner. An essential advantage of the present invention is thus that a process or system for processing a plurality of alarms at a production site can be adapted in a simple manner to properties, to conditions to be taken into consideration and to requirements of the production site, without changes having to be made for this in the individual hardware components.

It is, above all, possible for a user to implement and to operate an alarm management system, in which an automated and reliable prioritization of the alarm takes place despite the simultaneous occurrence of a plurality of alarms, so that suitable actions can be taken rapidly and as needed.

At the same time, the effort needed for the people working at a central office of a production site, such as a shift leader, dispatcher or factory fire department is reduced and the safety of the people working in the different work areas at the production site increases. It is essential for the solution according to the present invention in this connection that a hazard potential is determined for each alarm event on the basis of weighted influencing variables, so that the different hazard potentials can be compared with one another in case of simultaneously occurring alarms and a reliable prioritization of the individual alarm situations can be carried out for taking suitable actions.

While specific embodiments of the invention have been shown and described in detail to illustrate the application of the principles of the invention, it will be understood that the invention may be embodied otherwise without departing from such principles.

LIST OF REFERENCE NUMBERS

1 Data processing unit
2 Data analysis unit
3 Gas measuring device
   3a Mobile gas measuring device
   3b Stationary gas measuring device
4 Central memory
5 transmission interface of the data processing unit

What is claimed is:

1. A process for an analysis of data provided by a mobile gas measuring device, the process comprising the steps of:
   generating measured data, by the mobile gas measuring device, based on at least one measurement of a gas concentration in a monitored area;
   transmitting the measured data to an additional mobile gas measuring device or to a central data processing unit or to an additional mobile gas measuring device and to a central data processing unit;
   comparing the measured data with a limit value stored in any of the mobile gas measuring device, the additional gas measuring device and the central data processing unit to determine if there is a limit value violation comprising an inadmissible overshooting or undershooting of the limit value;
   generating an alarm control signal, suitable for taking an action, by any of the mobile gas measuring device, the additional gas measuring device and the central data processing unit, for the limit value violation;
   determining a hazard potential in any of the mobile gas measuring device, the additional gas measuring device and the central data processing unit in case of a determined limit value violation, taking into consideration weighted influencing variables;
   assigning the hazard potential determined to the limit value violation;
   upon a first limit value violation and at least one second limit value violation being determined during a common time period or during overlapping time periods, comparing hazard potentials of the first limit value violation and of the at second limit value violation to one another to determine a prioritization of limit value violations based on comparing hazard potentials,
   wherein the generation of the alarm control signals for the first limit value violation and for the at least one second limit value violation is carried out based on the determined prioritization of limit value violations.

2. A process in accordance with claim 1, further comprising displaying action recommendations, based on the generated alarm control signals, by the central data processing unit, on a display unit corresponding to the prioritization.

3. A process in accordance with claim 1, further comprising sending the alarm control signal to the mobile gas measuring device by the central data processing unit based on the prioritization determined.

4. A process in accordance with claim 1, further comprising outputting one or more of an optically perceptible alarm, an acoustically perceptible alarm and a haptically perceptible alarm based on the alarm control signal.

5. A process in accordance with claim 1, wherein at least one of the mobile gas measuring device and the additional gas measuring device generate the alarm control signal and output an alarm based on the alarm control signal.

6. A process in accordance with claim 1, further comprising sending a request signal to rescue team members based on the determined hazard potential or the determined prioritization or both the determined hazard potential and the determined prioritization.

7. A process in accordance with claim 1, wherein, based on the determined hazard potential or the determined prioritization or both the determined hazard potential and the determined prioritization, at least one of:
   activating a safety device;
   placing a machine out of operation;
   placing a plant out of operation; and
   blocking an area.

8. A process in accordance with claim 1, wherein the weighted influencing variables comprise one or more of: a maximum magnitude of a measured value; a change over time of a measured value; a toxicity of a substance to be expected to be present in the monitored area; operating parameters of a plant arranged in the monitored area; operating parameters of a machine arranged in the monitored area, an immediately dangerous to life and health (IDLH) state; a time period elapsed since a measurement; a detection of a limit value violation and a time period elapsed since a generation of an alarm control signal; personal data of a measuring device user; motion data of the mobile gas measuring device; fire extinguishing devices available in the monitored area; fan devices available in the monitored area; safety rooms available in the monitored area; protective equipment available in the monitored area; a number of alarms in the monitored area; a number of alarms in an area of the monitored area; a distance between a location of a measurement and available rescue team members; and a number and an arrangement of available escape routes.

9. A system for measuring a concentration of a gas in a monitored area, the system comprising:
   mobile gas measuring devices generating measured data;
   a central data processing unit; and
   transmission means for a unidirectional or bidirectional data transmission between the mobile gas measuring devices and the central data processing unit, the transmission means transmitting measured data from one of the mobile gas measuring devices to the other of the mobile gas measuring devices or to the central data processing unit or to the other of the mobile gas measuring devices and to the central data processing unit, wherein the system is configured to:
   compare the measured data with a limit value, stored in any of the mobile gas measuring devices and the central data processing unit, to determine if there is a limit value violation comprising an inadmissible overshooting or undershooting of the limit value;
   generate an alarm control signal suitable for taking an action by any of the mobile gas measuring device, the additional gas measuring device and the central data processing unit, for the limit value violation;

determine a hazard potential in any of the mobile gas measuring device, the additional gas measuring device and the central data processing unit in case of a determined limit value violation, taking into consideration weighted influencing variables;

assign the hazard potential determined to the limit value violation;

upon a first limit value violation and a second limit value violation being determined during a common time period or overlapping time periods, compare hazard potentials of the first limit value violation and of the second limit value violation to one another to determine a prioritization of limit value violations based on comparing hazard potentials;

wherein the generation of the alarm control signals for the first limit value violation and for the second limit value violation are carried out based on the determined prioritization of limit value violations.

10. A system in accordance with claim 9, further comprising a display unit, wherein the system is configured to display action recommendations, based on the generated alarm control signals by the central data processing unit, on the display unit corresponding to the prioritization.

11. A system in accordance with claim 9, wherein the central data processing is configured to send the alarm control signal to the mobile gas measuring device, via the transmission means, based on the prioritization determined.

12. A system in accordance with claim 9, further comprising means for outputting one or more of an optically perceptible alarm, an acoustically perceptible alarm and a haptically perceptible alarm based on the alarm control signal.

13. A system in accordance with claim 9, wherein at least one of the mobile gas measuring device and the additional gas measuring device generate the alarm control signal and output an alarm based on the alarm control signal.

14. A system in accordance with claim 9, wherein the system is configured to send a request signal to rescue team members based on the determined hazard potential or the determined prioritization or both the determined hazard potential and the determined prioritization.

15. A system in accordance with claim 9, wherein, based on the determined hazard potential or the determined prioritization or both the determined hazard potential and the determined prioritization, the system is configured to at least one of:
activate a safety device;
place a machine out of operation;
place a plant out of operation; and
block an area.

16. A system in accordance with claim 9, wherein the weighted influencing variables comprise one or more of: a maximum magnitude of a measured value; a change over time of a measured value; a toxicity of a substance to be expected to be present in the monitored area; operating parameters of a plant arranged in the monitored area; operating parameters of a machine arranged in the monitored area, an immediately dangerous to life and health (IDLH) state; a time period elapsed since a measurement; a detection of a limit value violation and a time period elapsed since a generation of an alarm control signal; personal data of a measuring device user; motion data of the mobile gas measuring device; fire extinguishing devices available in the monitored area; fan devices available in the monitored area; safety rooms available in the monitored area; protective equipment available in the monitored area; a number of alarms in the monitored area; a number of alarms in an area of the monitored area; a distance between a location of a measurement and available rescue team members; and a number and an arrangement of available escape routes.

17. An alarm management system for managing alarms, the alarm management system comprising:
mobile gas measuring devices carrying out gas concentration measurements in a monitored area;
alarm triggering means for triggering alarms based on a determination of limit value violations caused by overshooting or undershooting of a limit value during the measurement of gas concentrations in the monitored area; and
a central data processing unit configured to:
determine a hazard potential for the limit value violations determined, wherein the hazard potential is based on the measurement and an analysis, taking into consideration weighted influencing variables;
assign the determined hazard potential to the limit value violations;
upon the limit value violations, including a first limit value violation and a second limit value violation, being determined during a common time period or overlapping time periods, comparing the hazard potential assigned to the first limit value violation and the hazard potential assigned to the second limit value violation to one another and determining a prioritization of the first limit value violation and the second limit value violation based on the comparison; and
generate an alarm control signal, suitable for taking an action, for the first limit value violation and for the second limit value violation, wherein the alarm control signals are generated taking into consideration the determined prioritization.

18. An alarm management system according to claim 17, further comprising a control room of a refinery, of an industrial production plant, a mine or a power plant.

* * * * *